(12) United States Patent
Dorignac et al.

(10) Patent No.: US 11,118,157 B2
(45) Date of Patent: Sep. 14, 2021

(54) YEAST STRAINS FOR FERMENTED DRINKS, PARTICULARLY WINE

(71) Applicant: LESAFFRE ET COMPAGNIE, Paris (FR)

(72) Inventors: Etienne Dorignac, Mazeres (FR); Anne-Dominique Quipourt, Marc en Baroeul (FR); Annie Tbaikhi, Wambrechies (FR)

(73) Assignee: LESAFFRE ET COMPAGNIE, Paris (FR)

( * ) Notice: Subject to any disclaimer, the term of this patent is extended or adjusted under 35 U.S.C. 154(b) by 98 days.

(21) Appl. No.: 15/760,250

(22) PCT Filed: Sep. 20, 2016

(86) PCT No.: PCT/FR2016/052385
§ 371 (c)(1),
(2) Date: Mar. 15, 2018

(87) PCT Pub. No.: WO2017/051114
PCT Pub. Date: Mar. 30, 2017

(65) Prior Publication Data
US 2018/0251863 A1 Sep. 6, 2018

(30) Foreign Application Priority Data
Sep. 21, 2015 (FR) ...................... 15 58875

(51) Int. Cl.
| | | |
|---|---|---|
| *C12R 1/85* | (2006.01) | |
| *C12N 1/16* | (2006.01) | |
| *C12N 1/18* | (2006.01) | |
| *C12G 1/022* | (2006.01) | |
| *C12R 1/865* | (2006.01) | |

(52) U.S. Cl.
CPC ........... *C12N 1/185* (2021.05); *C12G 1/0203* (2013.01); *C12N 1/16* (2013.01); *C12N 1/18* (2013.01); *C12G 2200/05* (2013.01); *C12G 2200/11* (2013.01); *C12R 2001/85* (2021.05); *C12R 2001/865* (2021.05)

(58) Field of Classification Search
CPC ......... C12R 1/85; C12R 1/865; C12G 1/0203; C12G 2200/05; C12G 2200/11; C12N 1/16; C12N 1/18
See application file for complete search history.

(56) References Cited

PUBLICATIONS

Gonzalez, S. S., et al., Natural hybrids from *Saccharomyces cerevisiae*, *Saccharomyces bayanus* and *Saccharomyces kudriavzevii* in wine fermentations, 2006, Federation of European Microbiological Societies, 6, 1221-1234 (Year: 2006).*
Laffort Vintage 2015 Catalogue, Jul. 7, 2015 (Year: 2015).*
Gutierrez, A. et al., Nitrogen requirements of commercial wine yeast strains during fermentation of a synthetic grape must, 2012, Food Microbiology, 31, 25-32 (Year: 2012).*
Marullo, P., et al., Breeding strategies for combining fermentative qualities and reducing off-flavor production in a wine yeast model, 2006, FEMS Yeast Research, 6, 268-279 (Year: 2006).*
Luc Laffort, "Laffort Vintage 2015", Laffort, XP-002758086, 102 pages.
International Search Report for PCT/FR2016/052385, dated Jan. 18, 2017.

* cited by examiner

*Primary Examiner* — Louise W Humphrey
*Assistant Examiner* — Anjali Ajit Hirani
(74) *Attorney, Agent, or Firm* — Sughrue Mion, PLLC

(57) ABSTRACT

The present invention relates to a yeast strain likely to be obtained by hybridizing a strain S1 with a strain S2, said yeast strain presenting, according to test A, the following characteristics:
fermentation kinetics from 15 to 22 days at a temperature of 24° C.; and
resistance with an alcoholic strength of more than or equal to 15% v/v; and
a nitrogen requirement of less than or equal to 200 ppm, to the method of producing this strain and to its use.

5 Claims, 1 Drawing Sheet

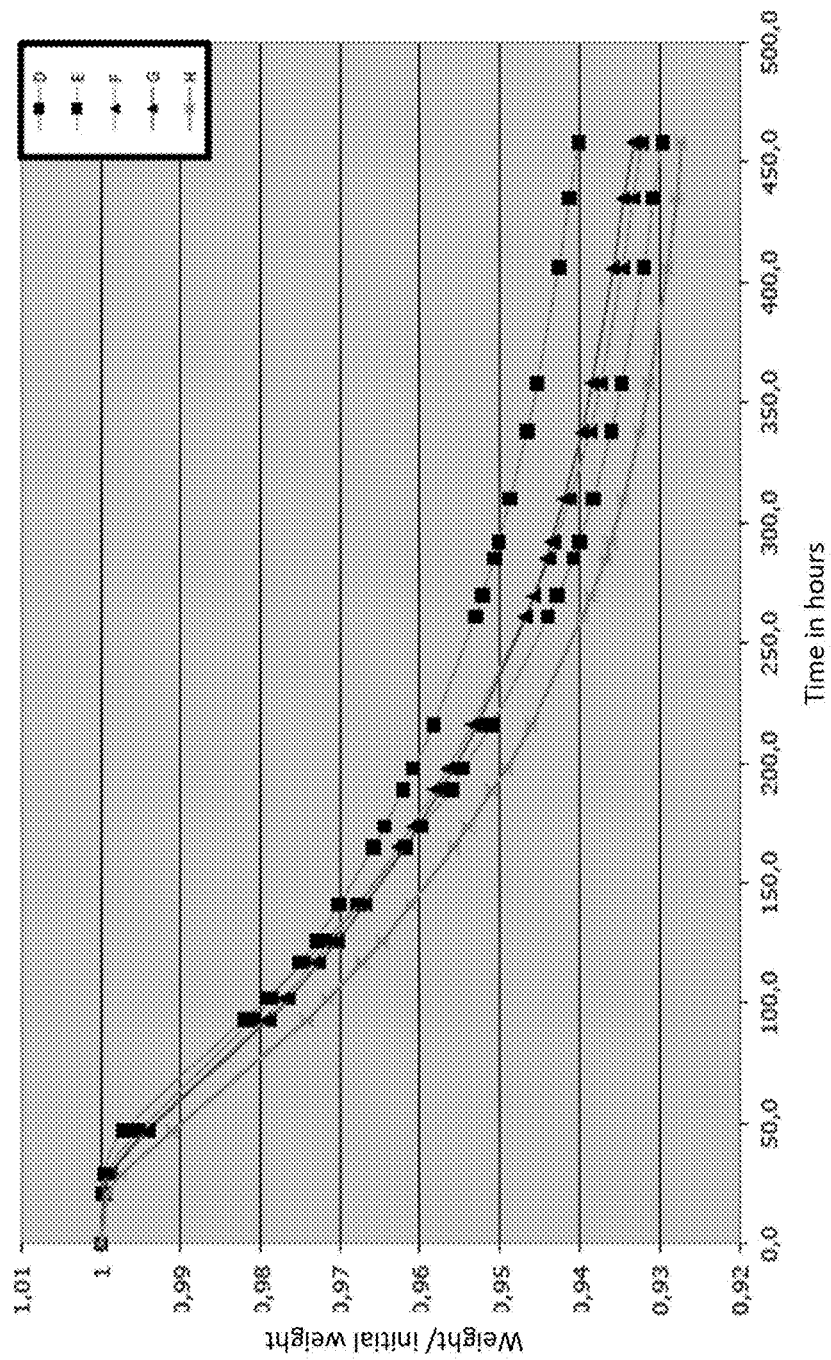

YEAST STRAINS FOR FERMENTED DRINKS, PARTICULARLY WINE

CROSS REFERENCE TO RELATED APPLICATIONS

This application is a National Stage of International Application No. PCT/FR2016/052385 filed Sep. 20, 2016, claiming priority based on French Patent Application No. 15 58875 filed Sep. 21, 2015.

TECHNICAL FIELD OF THE INVENTION

The present invention relates to yeast strains for fermented drinks as well as methods of selecting said strains. The present application also relates to the use of yeasts from these strains to produce wine.

TECHNOLOGICAL BACKGROUND

Fermentation is one of the essential steps in wine production, during which the sugars present in grape must are transformed into alcohol via the action of microorganisms such as yeasts.

Different yeast strains are used depending on the type of wine produced. The *Saccharomyces* S1 yeast strain, from the applicant, has the ability to ferment regularly but very slowly: this strain is therefore particularly suitable for premium-quality red wines resulting from a long maceration/extraction process in order to benefit from the high levels of polyphenols (anthocyanins, tannins) in highly-colored and very tannic black grape varieties.

Unfortunately, this strain has difficulty fermenting musts with an alcohol potential greater than 14% v/v in the presence of a normal or even high quantity of nitrogen available in the must. These conditions are common for red wines intended to be reserve wines, which by their nature have a high alcohol potential and result from overripe grapes producing musts lacking available nitrogen. Therefore, under these conditions, there is a high risk of the fermentation stopping prematurely, which is harmful to wine production.

Therefore it would be especially advantageous to develop means enabling the fermentation abilities of yeast strain S1 to be improved, so as to make it more interesting in vinification.

Yeasts can be improved either by using conventional genetic techniques or by using molecular genetic techniques. However, the vinification market is very resistant to using genetically modified microorganisms (GMO).

INVENTION

Thus, the inventors have determined that it was possible to obtain a strain that is of particular interest in the vinification of black grapes with high tannin levels by hybridizing the strain S1 with a yeast strain capable of quickly fermenting a large quantity of sugars in the presence of a small quantity of nitrogen and at a low temperature: The S2 yeast strain of the *Saccharomyces bayanus* species belonging to the applicant.

Thanks to this hybridization process, the inventors produced and selected several strains that present very good fermentation kinetics and tolerance to an alcoholic strength of more than 15% v/v and fermentation ability in the presence of a small quantity of available nitrogen. These strains find particular interest in the vinification of musts low in available nitrogen that require long fermentation, which is the case with wines known as "reserve" wines, such as the great vintages of Bordeaux.

Therefore, according to a first aspect, the invention relates to a yeast strain obtainable by hybridizing a strain S1 with a strain S2, said yeast strain presenting, according to a test A as defined below, the following characteristics:
- fermentation kinetics from 15 to 22 days at a temperature of 24° C.; and
- tolerance to an alcoholic strength of more than or equal to 15% v/v; and
- a nitrogen requirement of less than or equal to 200 ppm.

The inventors have also developed a method which allows obtaining and selecting wine yeast strains from the hybridization of a strain S1 with a strain S2.

Therefore, according to another aspect, the present invention relates to a method of obtaining a wine yeast strain, said method comprising the following steps:
a) hybridizing a yeast strain S1 with a yeast strain S2;
b) isolating the strains obtained in step a);
c) seeding the strains isolated in step b) on a must;
d) studying the fermentation kinetics of said strains; and
e) selecting the strains presenting fermentation kinetics at least 15%, preferably at least 30%, more preferentially at least 40% greater than the parent strain S1 and at least 15%, preferably at least 30%, more preferentially at least 40% lower than the parent strain S2 on the same must as that of step c).

The invention also relates to the use of a yeast strain as described above for producing fermented drinks and, more specifically, wine.

DETAILED DESCRIPTION OF THE INVENTION

To improve the wine-growing abilities of yeast strain S1, particularly its fermentation abilities, the inventors developed novel strains specifically adapted to wine-growing use.

Here "improved fermentation characteristics" is understood to mean yeast strains that have the advantages provided by the strain S1, especially an ability to ferment a must at a moderate and regular speed, without analytical faults such as average volatile acidity production and low $SO_2$ production and with interesting organoleptic characteristics such as enhanced polyphenol extraction and the promotion of fruity aromas but which can also ferment quickly, possibly in the presence of a moderate quantity of available nitrogen, and in a prolonged manner (even when the alcoholic strength of the must exceeds 15% v/v).

Therefore the selection criteria retained here are the following:
- higher fermentation kinetics than that of the parent strain S1 but equally regular as the latter; and
- an ability to ferment in the presence of a moderate quantity of available nitrogen; and Tolerance to a high alcoholic strength (i.e., equal to or more than 15%).

Therefore, a first aspect of the invention relates to a yeast strain likely to be obtained by hybridizing a strain S1 with a strain S2, said yeast strain presenting, according to test A, the following characteristics:

i) fermentation kinetics from 15 to 22 days at a temperature of 24° C.; and ii) tolerance to an alcoholic strength of more than or equal to 15% v/v; and iii) a nitrogen requirement of less than or equal to 200 ppm.

"Test A" according to the present invention is a test following the fermentation activity of yeast strains that are seeded in the amount of $2.10^6$ CFU/ml on a synthetic must standardized by the International Organisation of Vine and Wine [Organisme International de la Vigne et du Vin—OIV] (OIV-OENO RESOLUTION 370-2012) adjusted to 250 g/l of fermentable sugars (to obtain an alcohol potential of 15% v/v) with an initial nitrogen concentration of 200 ppm by fermenting at a constant temperature of 24° C.

The expression "Yeast strain" means a relatively homogeneous population of yeast cells. A yeast strain is obtained from a clone, a clone being a population of cells obtained from a single yeast cell.

"Wine yeast strain" is understood to refer to a strain that is used for fermenting wine.

The yeast strain S1 or strain S1 refers to the yeast strain of the applicant deposited on Sep. 9, 2015 at the National Collection of Microorganism Cultures (Collection Nationale de Cultures de Microorganismes—CNCM)—Institut Pasteur, 25 rue du docteur Roux F75724 Paris under reference I-5011.

The yeast strain S2 or strain S2 refers to the yeast strain in the name of the applicant deposited on Sep. 9, 2015 at the CNCM under reference I-5012.

"Tolerance to an alcoholic strength of equal to or more than X % v/v" means that the yeast strain is capable of surviving and continuing to ferment when the alcoholic strength by volume of the medium is of more than or equal to X % v/v.

The "nitrogen requirement" of a yeast strain is defined by the minimum quantity of available nitrogen that must be present in the must so that said strain can complete the fermentation (presence of at least 2 g/l of residual fermentable sugars) on a given must.

The fermentation kinetics can be easily measured by various techniques known to the person skilled in the art. For example, the fermentation kinetics can be measured by tracking fermentation by means of weighing over time.

The invention particularly relates to two novel yeast strains as described above: strains 51-062 and 51-135 filed on 5 May 2015 at the CNCM pursuant to the Budapest Treaty under numbers I-4975 and I-4977 respectively.

The invention also relates to yeast isolated from a yeast strain as described above.

The inventors have also developed a process of hybridizing strain S1 with the *Saccharomyces bayanus* S2 strain, a strain that has the ability to ferment a large quantity of sugars rapidly in the presence of a small amount of nitrogen at a low temperature. Then, they have developed a selection process enabling to identify, among the various strains obtained from this hybridization, strains presenting fermentation characteristics that are improved, and which are therefore of interest in vinification.

Therefore, in another aspect, the invention relates to a method of obtaining a wine yeast strain, said method comprising the following steps:

a) hybridization of a yeast strain S1 with a yeast strain S2;

b) isolation of the strains obtained in step a);

c) seeding the strains isolated in step b) on a must;

d) studying the fermentation kinetics of said strains; and e) selecting the strains presenting fermentation kinetics at least 15%, preferably at least 30%, more preferentially at least 40% greater than the parent strain S1 and at least 15%, preferably at least 30%, more preferentially at least 40% lower than the parent strain S2 on the same must as that of step c).

The person skilled in the art knows several methods of hybridizing yeast strains and would be able to use a suitable method for hybridizing yeast strain S1 to yeast strain S2. In the present case, the inventors discovered that the strain S1 cannot produce sexual type spores differentiated a or alpha; this strain is therefore homothallic. Therefore, a means of hybridizing the strain S1 with the strain S2 would consist of hybridization of spores from these two strains following the dissection of tetrads from each strain. The new hybrid can thus be the result of crosses between a spore from S1 with a spore from S2 or rather the result of crosses between a spore S1 with a spore from S1 in which the sexual type has changed during replication. Hybrids obtained from crosses between a spore from S1 and a spore from S2 are subsequently selected by analyzing the genetic profiles of the new hybrids (for example by PCR Ty), and comparing these profiles with the genetic profiles of parent strains.

Here "must" is understood to refer to grape must, i.e., the mixture obtained after pressing grapes or synthetic must, i.e., synthetically reconstituted so as to best imitate the composition of natural grape must.

Several musts can be used for the purposes of the present invention. By way of example, the synthetic "Lesaffre wine" must may be cited in order to preselect yeasts, the synthetic must standardized by International Organisation of Vine and Wine [Organisme International de la Vigne et du Vin—OIV] (OIV-OENO RESOLUTION 370-2012) to select yeasts or grape musts from black grape varieties that are concentrated in polyphenols either or not obtained from hot pre-fermentation maceration in order to put the yeasts in the environment for which they are intended to refine their selection.

In one embodiment, the fermentation test is carried out on a synthetic OIV must.

A "synthetic OIV must" is a synthetic must standardized by the International Organisation of Vine and Wine [Organisme International de la Vigne et du Vin—OIV] (OIV-OENO RESOLUTION 370-2012) adjusted to 250 g/l of fermentable sugars (to obtain an alcohol potential of 15% v/v) with an initial nitrogen concentration of 200 ppm.

Therefore, according to another embodiment, the present application relates to a method of obtaining a wine yeast strain, said method comprising the following steps:

a) hybridization of a yeast strain S1 with a yeast strain S2;

b) isolation of the strains obtained in step a);

c) seeding the strains isolated in step b) on a synthetic OIV must;

d) studying the fermentation kinetics of said strains; and e) selecting the strains presenting the following three characteristics:

i) fermentation kinetics from 15 to 22 days at a temperature of 24° C.; and ii) tolerance to an alcoholic strength of more than or equal to 15% v/v; and iii) a nitrogen requirement of less than or equal to 200 ppm.

The yeasts thus selected are capable of fermenting a large quantity of sugars by using a small amount of nitrogen, even at a high alcoholic strength.

In addition, according to another aspect, the invention relates to the use of a yeast strain or of a yeast as described above for producing wine, specifically red wine, still more specifically wine from a very tannic black grape variety. In another embodiment, the yeast strains and yeasts obtained/selected according to the present invention are used for fermenting red wines known as "reserve" wines.

A "reserve wine" is a wine that can be stored for several years in the cellar and that improves with age; this is the case with the great vintages of Bordeaux. A reserve wine can be stored at least five years in a cellar.

BRIEF DESCRIPTION OF THE FIGURES

FIG. 1 is a graph representing the fermentation kinetics of strains 51-062 (H), 51-135 (F), S1 (D) and S2 (E) and of one further hybrid strain (G) represented by measuring the weight/initial weight ratio as a function of time.

EXAMPLES

Example 1

Hybridization of Strains S1 with Those From S2

Sporulation of two parent strains and development of operational conditions for sporulating strain S1.

The sporulation conditions were applied to both S2 and S1 strains. The sporulation rates were calculated and are presented in Table 1.

TABLE 1

| Strain | % ascospores |
| --- | --- |
| Wine strain S2 | 13% |
| Wine strain S1 | 54% |

Isolation of spores by micromanipulation and study of the self-diploidization of spores isolted from strains S2 and S1.

The sporulation conditions were applied on a larger scale on the two wine strains. After treating asci and visualizing tetrads by microscope, a dissection consisting of breaking tetrads, removing spores and then depositing them on precise locations of the agar has been performed. The enumeration of deposited spores and germinated spores is presented in Table 2 below.

TABLE 2

| Strain | Number of dissected tetrads | Number of deposited spores | Number of germinated spores | Germination Rates |
| --- | --- | --- | --- | --- |
| S2 | 50 | 200 | 73 | 36% |
| S1 | 33 | 132 | 95 | 72% |

To be able to hybridize between strain S2 and S1, sexual type spores clearly differentiated a or alpha must be obtained for each strain. The sexual sign of each spore previously obtained was studied by PCR "mating type" (Table 3).

TABLE 3

| Strain | Number of germinated spores | Sign a | Sign alpha | Sign a/alpha | No result |
| --- | --- | --- | --- | --- | --- |
| S2 | 39 | 20 | 14 | 4 | 1 |
| S1 | 95 | 0 | 0 | 95 | 0 |

Table 3 shows that sexual type spores differentiated a or alpha could not be obtained for strain S1. Therefore it appears that strain S1 is homothallic. Under these conditions, contemplating a conventional hybridization program between strains S2 and S1 is not possible.

Developing hybridization operating conditions specific to the S1×S2 crossing, isolating the new strains and studying their genetic profile to select the hybrids obtained from the crossing between S1 and S2.

The inventors, having no collection of sexual type a or alpha spores for strain S1 available, have hybridized spores from S1 and S2 following the dissection of tetrads from each strain via the micromanipulator. The new hybrid can therefore be the result of crosses between a spore from S1 with a spore from S2 or rather the result of crosses between a spore from S1 with a spore from S1 in which the sexual type has changed during replication. in order to select hybrids obtained from the cross between a spore from S1 and a spore from S2, the genetic profiles of the new hybrids were analyzed by PCR Ty, and these profiles were then compared to that of the parent strains. Finally, 68 hybrids presenting mixed profiles at different strengths in relation to the parent strain profile were retained. The oenological qualities of these 68 strains were then evaluated. Strains 51-062 and 51-135 were selected as follows.

Example 2

Development of Hybrid Selection Techniques

Several selection techniques were used:

a) Selection in synthetic conditions by studying fermentable sugar dehydration, fermentation kinetics and the production of fermentation compounds of interest in hybrids and parent strains on synthetic Lesaffre wine must (250 g/L sugars and 250 ppm available nitrogen)=test A and synthetic OIV must.

A first selection, done on the kinetics criterion, enabled the selection of 11 hybrids presenting better properties than S1 in terms of fructose dehydration.

Among these hybrids, strains 51-062 and 51-135 were selected because they present average kinetics between S1 and S2 and at the end of fermentation, these strains produce intermediate fermentation compounds that are different from the two parent strains.

b) Selection in real conditions by studying fermentation kinetics and ester production on natural musts of hybrids and parent strains:

The selection criterion was the analysis of fermentation kinetics, control of oenological parameters and principal ester analysis during microvinifications on natural Cabernet Sauvignon must. This must is obtained by hot pre-fermentation maceration of very ripe cabernet sauvignon grapes. The must from this year's harvest has been stored at −60° C. in the freezer.

Before fermentation, the must was processed in the following manner: 1) Thawing at room temperature, 2) Clarification by centrifugal separation 3) Separation of the must into 5 homogeneous batches.

Before fermentation, the must was analyzed by Fourier transform infrared spectroscopy+colorimetric $SO_2$ determination. The results obtained are summarized in Table 4 below:

TABLE 4

| Glucose + fructose (g/L) | Total acidity (g eq H2SO4/L) | pH | Malic acid (g/L) | Tartaric acid (g/L) | Citric acid (g/L) | K (mg/L) | NH3 (mg/L) | NOPA (mg/L) | $SO_2$L (mg/L) | $SO_2$ T (mg/L) |
|---|---|---|---|---|---|---|---|---|---|---|
| 246 | 4.30 | 3.34 | 3.38 | 1.8 | 0.66 | 670 | 42 | 103 | 0 | 0 |

Following the must analysis, the absence of alcohol and acetic acid before fermentation were also observed. 246 g of Glucose+fructose corresponding to a probable strength of 14.6% vol (yield of 16.83).

Preparations of yeasts on agar tubes: strains 51-135 (F) and 51-062 (H)

Preparation of the medium to be incubated on Day 0: Yeast extract 20 g, Sucrose 100 g, Mineral solution (100 g MgSO4+100 g KH2PO4+Demineralized water QS 1 L) 10 mL, Tap water QS 1 L.

On Day 3—inoculation of test tubes "A" (for each strain tested): A monosaccharide is removed from the agar and deposited in 10 ml of medium to be incubated for 24 hours at 26° C.

On Day 4—preparation of test tubes "B" 1 ml from tube A in 9 ml of medium to be incubated 24 hours at 26° C.

On Day 5: Pour each tube "B" into 90 ml of medium to be incubated 16 hours+/−2 hours at 26° C. with good agitation.

On Day 6: Measuring the population with a Thoma cell.

Seeding jars (Table 5):

TABLE 5

| Preparation | Yeasts/ large square | Yeasts/ mlx1.6.10$^5$ | Yeasts/ 100 mL | Volume seeded in a jar | Estimated population cell/L |
|---|---|---|---|---|---|
| F (strain 51-135) | 152 | 2.10$^7$ | 2.10$^9$ | 100 mL | 2.10$^8$ |
| H (strain 51-062) | 173 | 3.10$^7$ | 3.10$^9$ | 100 mL | 3.10$^8$ |

Control of the population in jars (Table 6):

TABLE 6

| Preparation | Yeasts/Large square | Cell population/L |
|---|---|---|
| F (strain 51-135) | 13 | 2.10$^9$ |
| H (strain 51-062) | 16 | 3.10$^9$ |

Preparation of dry yeasts: strains D (strain S1) and E (strain S2):

On Day 6: Hydration of yeasts in sterile water: 1 g in 10 mL and then ultrasonic agitation for 10 minutes, incubation at 30° C. for 20 minutes, ultrasonic agitation for 15 minutes, rest 20 minutes at ambient temperature.

The jars were seeded at 2 ml of preparation in 1 L of must. The population was verified with a Thoma cell: 10$^{10}$ cell/L (Table 7):

TABLE 7

| Preparation | Yeasts/Large square | Cell population /L |
|---|---|---|
| D (strain S1) | 35 | 6.10$^9$ |
| E (strain S2) | 34 | 5.10$^9$ |

Fermentation Analyses

Fermentations are conducted in a climate-controlled room with a temperature of 18° C. The fermentation kinetics are analyzed by weighing jars on a +/−0.1 g scale, approximately 2 times/day. Fermentation started on Day 7 and stopped on Day 19.

The results are presented in FIG. 1.

At the end of fermentation: Racking and sulfuring around 60 mg/L, bottling and storage at 8° C.

Analyses on Resulting Wines

Analysis by Fourier transform infrared spectroscopy and colorimetric SO2 determination on D20:

TABLE 8

|   | Total alcoholic strength by volume % v | Glucose + fructose (g/L) | Total alcoholic strength by volume % v | Total acidity (gH$_2$SO$_4$/L) | Acetic acid (g/L) | Free SO2 (mg/L) | Total SO2 (mg/L) | pH | Malic acid (g/L) | Lactic acid g/L |
|---|---|---|---|---|---|---|---|---|---|---|
| D | 15.13 | 18   | 16.2 | 4.94 | 0.62 | 10 | 72 | 3.51 | 2.1 | 0 |
| E | 12.74 | 54   | 15.9 | 4.81 | 0.6  | 10 | 58 | 3.34 | 2.0 | 0 |
| F | 14.64 | 23   | 16   | 5.12 | 0.71 | 12 | 74 | 3.51 | 2.4 | 0 |
| H | 15.39 | 12.9 | 16.2 | 4.81 | 0.48 | 10 | 44 | 3.51 | 2.1 | 0 |

Depending on the yeast strain, the following is observed:
0.5% volume variance on the total alcoholic strength by volume.
After 19 days, residual sugars are present for all strains.
total acidity varies from 4.69 to 5.12 g eqH2SO4/L
volatile acidity varies from 0.48 to 0.71 g eqH2SO4/L
The malolactic fermentation did not begin.
Polyphenol color analysis (Table 9)

|   | Color intensity | Shade | DO280 |
|---|---|---|---|
| D | 13.8 | 0.58 | 54 |
| E | 17.9 | 0.67 | 59 |
| F | 13.5 | 0.61 | 56 |
| H | 14.8 | 0.60 | 55 |

Ester Analysis

| Sample | Ethyl butyrate (µg/L) | Ethyl-2-methylbutyrate (µg/L) | Ethyl Isobutyrate (µg/L) | Ethyl Levulinate (µg/L) | Ethyl Isovalerate (µg/L) | Ethyl Hexanoate (µg/L) | Ethyl Octanoate (µg/L) | Ethyl Decanoate (µg/L) | Ethyl-2-Hydroxy-4-methylpentanoate (µg/L) | Isoamyl Acetate (µg/L) |
|---|---|---|---|---|---|---|---|---|---|---|
| D | 170.2 | <5 | <5  | <20 | <5 | 254.5 | 349.8 | 339.3 | 168.3 | 609.4 |
| E | 128.6 | <5 | <5  | <20 | <5 | 253.3 | 466   | 473.8 | 84.5  | 484   |
| F | 219.9 | <5 | 5   | <20 | <5 | 279   | 441.3 | 366.1 | 201   | 436.2 |
| H | 276   | <5 | 7.1 | <20 | <5 | 386.5 | 567.5 | 447.6 | 211.5 | 523   |

CONCLUSION

In general, we observe no significant difference between the results produced by dry yeast D and those produced by agar tube yeasts.

|   | Active dry yeasts | Agar tube yeasts |
|---|---|---|
| Total alcoholic strength | No significant difference | |
| Residual sugars | Presence of residual sugars <30 g/L Stop fermentation | |
| Volatile acidity | No significant difference except with "H" = 0.48 | |
| Malolactic fermentation | Not done | |
| Color intensity | 13.8 to 14.8 | |
| Shade | 0.58 to 0.65 | |
| DO280 | 54 to 56 | |

The hybrids confirm faster kinetics than S1 but 2 groups are formed:

51-135 shows intermediate fermentation kinetics compared to S2 and S1, residual contents of sugar and total SO2 (high therefore negative) and an influence on color close to S2 and an ester production slightly higher but close to the parent yeasts.

51-062 shows faster kinetics than S2 but with an equivalent slope, residual sugar content, volatile acidity and SO2 lower than S2 and higher ester production than the parent strains. This yeast does not appear to correspond to the kinetic criterion but presents very interesting characteristics that should be subject to further study.

The invention claimed is:

1. Two yeast strains deposited at the National Collection of Microorganism Cultures under number I-4975 and under number I-4977, obtained by hybridizing a strain S1 with a strain S2, wherein the strain S1 is deposited at the National Collection of Microorganism Cultures under number I-5011, and wherein the strain S2 is deposited at the National Collection of Microorganism Cultures under number I-5012.

2. A yeast cell isolated from one of the yeast strains obtained in claim 1, said yeast strains are deposited at the National Collection of Microorganism Cultures under number I-4975 and under number I-4977.

3. A method of obtaining an oenological yeast strain, said method comprising:
   a) hybridizing a yeast strain S1, deposited at the National Collection of Microorganism Cultures under number I-5011, with a yeast strain S2, deposited at the National Center of Microorganism Cultures under number I-5012;
   b) isolation of the strain produced after hybridization in step a);
   c) seeding of the strain isolated in step b) on a synthetic must;
   d) measuring the fermentation kinetics of said strain over 15 to 22 days of fermentation at a temperature of 24° C.; and
   e) selecting the strain presenting the following three characteristics:
      i) fermentation kinetics at least 15% greater than the parent strain S1 and at least 15% lower than the parent strain S2 on the synthetic must;
      ii) tolerance to an alcoholic strength of more than or equal to 15% v/v; and
      iii) a nitrogen requirement of less than or equal to 200 ppm.

4. A method for producing wine, comprising fermenting a must with one of the yeast strains obtained in claim 1, said yeast strains are deposited at the National Collection of Microorganism Cultures under number I-4975 and under number I-4977.

5. The method according to claim 4, wherein the wine is red wine.

* * * * *